(12) United States Patent
Plachter (10) Patent No.: US 6,713,070 B1
(45) Date of Patent: Mar. 30, 2004

(54) VIRAL PARTICLES WHICH ARE RELEASED AFTER THE INFECTION WITH THE HUMAN CYTOMEGALOVIRUS, AND THE USE OF SAID PARTICLES AS A VACCINE

(76) Inventor: Bodo Plachter, Lindenstrasse 17, D-55270 Klein-Winternheim (DE)

( * ) Notice: Subject to any disclaimer, the term of this patent is extended or adjusted under 35 U.S.C. 154(b) by 0 days.

(21) Appl. No.: 09/914,948

(22) PCT Filed: Mar. 2, 2000

(86) PCT No.: PCT/EP00/01794

§ 371 (c)(1),
(2), (4) Date: Sep. 6, 2001

(87) PCT Pub. No.: WO00/53729

PCT Pub. Date: Sep. 14, 2000

(30) Foreign Application Priority Data

Mar. 8, 1999 (DE) .......................... 199 10 044

(51) Int. Cl.$^7$ .................... A61K 39/245; A61K 39/385; A61K 39/00; A61K 39/295; A61K 39/12; C12Q 1/70

(52) U.S. Cl. ................................ 424/230.1; 424/192.1; 424/196.11; 424/202.1; 424/204.1; 424/230.1; 435/5

(58) Field of Search ......................... 424/192.1, 196.11, 424/193.1, 199.1, 202.1, 204.1, 230.1, 93.2; 435/235.1

(56) References Cited

FOREIGN PATENT DOCUMENTS

| WO | 98/26074 | | 6/1998 |
|----|----------|---|--------|
| WO | WO 98/26074 | * | 6/1998 |

OTHER PUBLICATIONS

Beninga et al. Journal of Infectious Diseases. 1996; 173 (5): 1051–1061.*

Pepperl–Klindworth, S., et al., "Protein delivery by subviral particles of human cytomegalovirus", *Gene Therapy*, 10:278–284 (2003).

Gibson, W., et al., "Selection of Particles and Proteins for Use as Human Cytomegalovirus Subunit Vaccines", *Birth Defects: Original Article Series, March of Dines Birth Defects Foundation*, 20(1): 305–324 (1984).

Sarov, I. ,et al., The Morphogenesis of Human Cytomegalovirus, Isolation and Polypeptide Characterization of Cytomegalovirus and Dense Bodies, *Virology*, 66: 464–473 (1975).

Jahn, G., et al., "The Two Major Structural Phosphoproteins (pp65 and pp150) of Human Cytomegalovirus and Their Antigenic Properties", *J. Gen. Virol.*, 68: 1327–1337 (1987).

Endresz, V., et al., "Induction of human cytomegalovirus (HCMV)–glycoprotein B (gB)–specific neutralizing antibody and phosphoproein 65 (pp65)–specific cytotoxic T lymphocyte responses to naked DNA immunization", *Vaccine*, 17: 50–58 (1999).

Wills, M., et al., "The Human Cytoxic T–Lymphocyte (CTL) Response to Cytomegalovirus is Dominates by Structural Protein pp65: Frequency, Specificity, and T–Cell Receptor Usage of pp65–Specific CTL", *Journal of Virology*, 70(11):7569–7579 (1996).

International Search Report, PCT/EP 00/01794, Sep. 6, 2000.

* cited by examiner

*Primary Examiner*—James Housel
*Assistant Examiner*—Shanon Foley
(74) *Attorney, Agent, or Firm*—Reed Smith (57) ABSTRACT

The invention relates to viral particles which are released by mammal cells after the infection with human cytomegalovirus (HCMV). The invention also relates to particles whose antigenicity has been optimized by changing the HCMV using genetic engineering. The invention further relates to the use of such particles as a vaccine and a method for multiplying the HCMV in mammal cells.

14 Claims, 8 Drawing Sheets

Figure 1:
Induction of neutralizing antibodies against HCMV after a single immunization with dense bodies

Figure 2:

Induction of neutralizing antibodies against HCMV after intraperitoneal immunization with native dense bodies three times

Figure 3:

Detection of long-lasting persistence of the neutralizing antibody response against HCMV after intraperitoneal immunization with native dense bodies three times

Figure 4:

Total cytolytic activity after immunization with native and disrupted DB

Figure 5:

HCMV-specific cytolytic activity of lymph node cells after immunization with native and disrupted DB Target cells: T2-A2.Kb Target cells: Jurkat A2.Kb — 20 µg of intact DB
· o · 2 µg of intact DB
— 20 µg of sonicated DB
— Contralateral lymph node Figure 6:
Analysis of lymphokine secretion from lymph node cells after immunization with native and disrupted DB

Figure 7:

Strategy for producing recombinant DB

Table 1:
Analysis of IgG subclasses in the serum of experimental animals as indicator of a Th1-typical or Th2-typical immune response after immunization with native or disrupted DB

| Serum sample | Anti-HCMV IgG1 | Anti-HCMV IgG2a | IgG1/IgG2a ratio |
|---|---|---|---|
| 12 weeks 3 x 20µg DB i.p. | 352 (±48) | 1639 (±210) | 0.21 |
| 32 weeks 3 x 20µg DB i.p. | 223 (±77) | 1277 (±123) | 0.17 |
| 32 weeks 3 x 20µg DB i.p. | 362 (±38) | 1365 (±150) | 0.26 |

An IgG1/IgG2 ratio of <1 indicates a Th1-typical immune response
An IgG1/IgG2 ratio of >1 indicates a Th2-typical immune response …

VIRAL PARTICLES WHICH ARE RELEASED AFTER THE INFECTION WITH THE HUMAN CYTOMEGALOVIRUS, AND THE USE OF SAID PARTICLES AS A VACCINE

This application claims priority to German Patent Application No. 19910044.6 filed Mar. 8, 1999.

The present invention relates to viral particles which are released after HCMV infection of mammalian cells, and to their use as vaccine.

Human cytomegalovirus (HCMV), a β-herpesvirus is a ubiquitously occurring pathogen. In an immunocompetent person, HCMV infection is normally unnoticed, having at the most mild and nonspecific symptoms. By contrast, in certain risk groups, for example in immunosuppressed patients such as AIDS patients or transplant recipients, and after prenatal infection, HCMV infection has serious manifestations.

Chemotherapeutics are available for treating HCMV infections. The success of antiviral chemotherapy of HCMV infection is restricted, however, in particular by the toxicity of the medicaments and the development of resistant variants of the virus if the duration of treatment is prolonged. In addition, the prophylactic or therapeutic use of antiviral hyperimmune sera has proved to be of only limited efficacy.

There has been work on the development of a vaccine against HCMV for many years. Thus, attempts have been made with weakened (attenuated) live vaccines to induce the desired immunity. This vaccine proved to have only limited efficacy, however. The reasons for this may be, inter alia, the restricted viability of such attenuated viruses in humans and strain-specific variations in the antigenicity. Besides the inadequacies in the induction of a permanent immunity, the use of a live vaccine must be regarded critically; lack of knowledge about the pathogenetic mechanisms in HCMV infection and the risk of reactivating the vaccine strain after immunosuppression make the use of a live vaccine appear at least questionable in these clinical situations.

In order to avoid these risks, strategies have recently been preferentially followed to develop subunit vaccines against HCMV which contain proteins from the viral envelope synthesized in various expression systems. Such envelope proteins, especially the glycoproteins gB and gH, are the essential target antigens of neutralizing antibodies against HCMV. Neutralizing antibodies are able to prevent the infection. It was possible both in experimental animals and in clinical studies to induce such neutralizing antibodies with a gB subunit vaccine. However, in humans, the antibody response induced in this way proved to be short-lived and not suitable for preventing the infection in all cases. This is detrimental to the wide use of subunit vaccines based exclusively on the gB of HCMV. The reasons which have been suggested for the limited efficacy of such antigen preparations in turn are the strain-specific variations in the immune response, lack of induction of an adequate cellular immune response, and structural restrictions of the antigen used, whose epitopes are in some cases known to be conformation-dependent.

On the basis of this experience, therefore, the requirements to be met by an effective and widely useful vaccine against HCMV are as follows:

(1) Long-lasting induction of neutralizing antibodies which protect from HCMV infection in a strain-overlapping manner. This requires efficient induction of a so-called "helper cell response" (CD4-positive T lymphocytes) against HCMV to assist the maturation of antibody-secreting B lymphocytes.

(2) Induction of the formation of cytotoxic T cells against HCMV. Lymphocytes of this type are of crucial importance for terminating an HCMV infection which has taken place and limiting the spread of the virus in the body.

(3) Minimizing the side effects by the vaccine. The risk which might derive from an inoculated viable virus which, according to present knowledge, would have the ability to establish latency after immunosuppression cannot be estimated. The aim ought therefore to be to prepare nonviable viral antigen as vaccine.

In order to comply with the conditions mentioned for an HCMV vaccine, the vaccine must contain the relevant antigens for inducing neutralizing antibodies and for stimulating helper cells ($T_H$ lymphocytes) and cytotoxic T cells (CTL).

Neutralizing antibodies are, according to the present state of knowledge, after HCMV infection formed exclusively against viral envelope proteins, and especially against the glycoproteins gB and gH.

$T_H$ cells are formed mainly against tegument proteins of the virus, and particularly against the so-called pp65 (ppUL83). In addition, pp65 is an essential antigen for the induction of CTL against HCMV. Presentation of pp65 takes place not only as usual after de novo synthesis by cells in connection with MHC class I molecules; it can also be introduced into the MHC I presentation pathway by so-called "exogenous loading".

Said antigens are the essential constituents of defective viral particles which, during the infection of primary human fibroblast cultures, are synthesized by HCMV and released into the culture medium. These so-called dense bodies (DB) are structures which are visible under the electron microscope and more than 90% of whose protein mass consists of pp65. They are comparable with virus particles in being provided with a cellular lipid membrane modified by viral glycoproteins and being ejected from the cell. The viral glycoproteins are very probably in the natural conformation in this envelope. Since DB contain no viral DNA and no viral capsid, they are non-infectious. They can be concentrated in large quantity from the cell culture supernatant by established methods.

One object of the invention was to provide an effective and widely usable vaccine against HCMV.

The present invention describes viral particles which are released after infection of mammalian cells by human cytomegalovirus (HCMV). These particles can be employed as preventive or therapeutic vaccine against infections by HCMV.

The particles of the invention are surrounded by a lipid membrane which makes it possible to fuse the particles to certain mammalian cells so that their contents enter the cytoplasm of the cells. The membrane of the particles contains viral glycoproteins which represent the main antigens for virus-neutralizing antibodies. The particles are also characterized in that they contain no viral DNA and no capsid. In addition, they contain the viral T-cell antigen pp65 (ppUL83) which both stimulates the formation of T-helper cells and is an essential antigen for inducing cytotoxic T lymphocytes (CTL) against HCMV.

These properties, especially the combination of antigens able to induce both neutralizing antibodies and an adequate cellular response, make the particles suitable as vaccines against HCMV.

Dense bodies have already been described in the literature (Gibson et al. Birth Defects: Original Article Series 20, 1 (1984) 305–324; Virology 66 (1975) 464–473). In this connection, their possible use as vaccine was suggested. However, no experiments proving that dense bodies in fact show the hoped-for effects were shown. In addition, it has been shown that dense bodies have an antigenic effect (Jahn et al., J. gen. Virol. 68 (1987) 1327–1337). However, these experiments do not characterize the induced immune response, which is why no information about the suitability as vaccine can be inferred.

The fact that the particles of the invention have a high antigenicity and are able to induce the formation of neutralizing antibodies is shown in examples 1 and 2. The induction of virus-neutralizing antibodies is long-lasting (example 3), which is another prerequisite for a successful vaccine. The immune response achieved in examples 1–3 is all the more surprising since the immunization was carried out without using adjuvant. Side effects of vaccines administered with adjuvants thus do not apply. The particles of the invention also activate cytotoxic T lymphocytes (CTL) (examples 4 and 5).

Finally, DB induce, irrespective of the route of administration, T-helper cell responses of the Th1 type (example 6).

These examples demonstrate that the particles of the invention are suitable as vaccine against HCMV.

In a further embodiment, particles which contain a fusion protein which comprises in one part one or more sections of the viral T-cell antigen pp65 (ppUL83) or the complete protein and in another part one or more sections of one or more other proteins are described.

This makes it possible to optimize the antigenicity of the particles because this fusion protein is present in large quantity in the particles. It is additionally known that expression of antigens of the cellular and humoral immune response in one molecule can distinctly increase the antigenicity. The various sections of pp65 and the other proteins can be fused together directly but it is also possible for example for linker sequences, which are not a natural constituent of one of the proteins involved, to be present between the various sections. Sequences of this type may arise because of the cloning or be introduced deliberately in order to influence the properties of the antigen. However, the fusion protein preferably contains no foreign sequences which are not a constituent of one of the fusion partners. In such embodiments, the fusion protein consists of one or more parts of pp65 and one or more parts of one or more other proteins.

It applies to all the embodiments mentioned hereinafter that the complete pp65 or one or more parts thereof can be present in the fusion protein. The statement "a fusion protein (consisting) of pp65" is not for the purposes of this application to be understood as restricted to complete pp65. A "part" or "section" of a protein present in the fusion protein comprises at least 6, preferably at least 8, most preferably at least 9, 15 or 20 consecutive amino acids of the protein from which it is derived.

Figure 7:
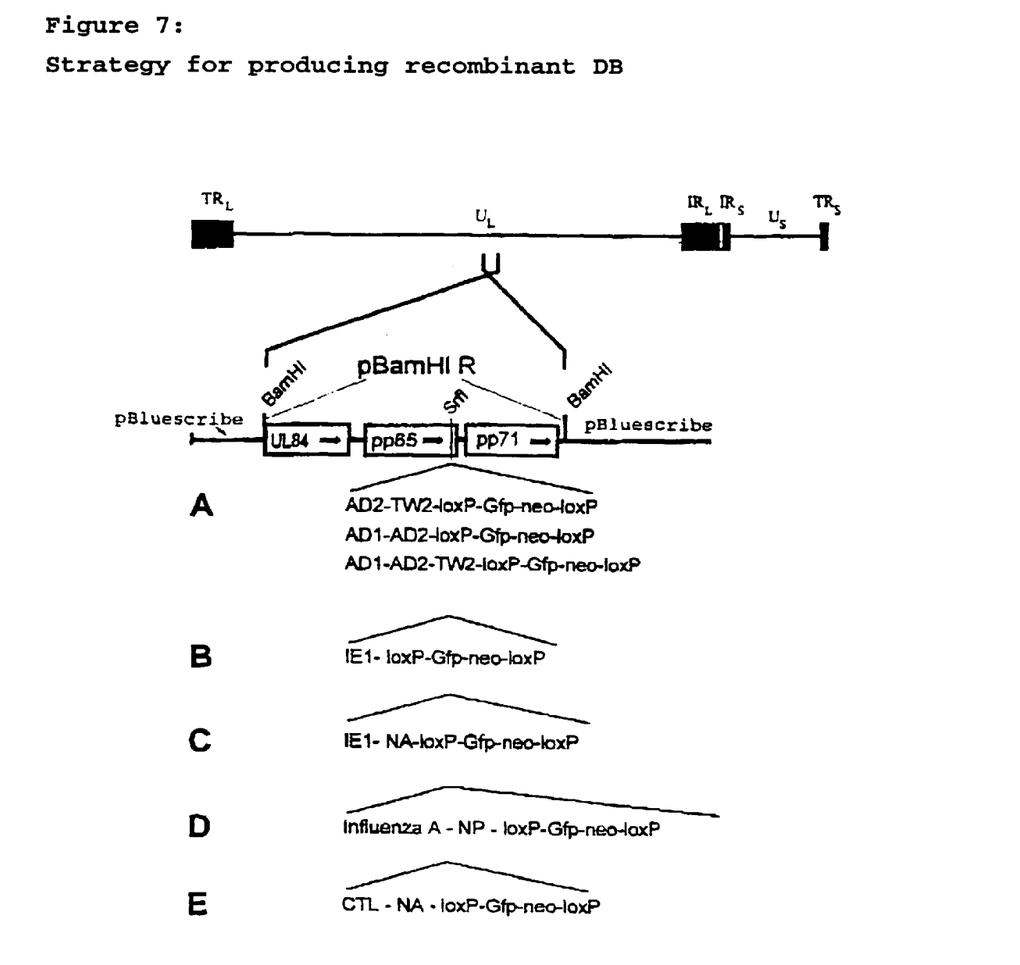
FIG. 7 shows the strategy for generating recombinant DB which contain fusion protein with homologous or heterologous antigens and which is described in example 8.

A preferred embodiment comprises a fusion protein of pp65 (ppUL83) and one or more neutralizing epitopes of the viral glycoproteins gB or gH. Particles of this type can be generated as depicted in FIG. 7A. The fusion protein can enter, via antigen-specific uptake, glycoprotein-specific B cells which in turn are able to present the epitopes both of the glycoproteins and of pp65 in the context of MHC class II. In addition, it is also possible for portions of the fusion protein to be presented by professional antigen-presenting cells (APC) in the context of MHC class II. In both cases the result is efficient stimulation of the $T_H$ response both to the pp65 and to viral glycoproteins. These $T_H$ cells are able to stimulate glycoprotein-specific B cells, which present peptides of pp65 and viral glycoproteins in the context of MHC class II, to form neutralizing antibodies both homologously and heterologously. In addition, particles of this type can, like infectious virions, be taken up into cells, and peptides of pp65 can be introduced by exogenous loading into the MHC class I pathway. This achieves, unusually for dead vaccines, a stimulation of the CTL response to HCMV.

In a further preferred embodiment, the particles contain a fusion protein consisting of pp65 and one or more parts of another protein of HCMV, the IE1 protein (ppUL123). The parts of the IE1 protein which are to be present in particular are those against which cytotoxic T cells are formed in humans during natural infection. Peptides of the IE1 protein are in some cases presented by different MHC class I molecules than are peptides of pp65. The addition of such further "CTL epitopes" from IE1 is intended to ensure that, after immunization, inoculated subjects who express different MHC class I molecules are able to generate CTL against HCMV in as comprehensive a manner as possible.

In a further preferred embodiment, the particles contain a fusion protein consisting of pp65, of one or more neutralizing epitopes of HCMV glycoproteins and of one or more CTL epitopes of IE1. Fusion of pp65 with neutralizing epitopes and CTL epitopes is intended to ensure that it is possible simultaneously for both neutralizing antibodies and CTL to be formed by inoculated subjects in as comprehensive a manner as possible, i.e. by the maximum number of people differing in MHC class I pattern.

In a further preferred embodiment, the particles contain a fusion protein of pp65 and one or more epitopes of another human pathogen. Suitable portions of other human pathogens are antigens against which neutralizing antibodies are formed in humans. It is possible through fusion of such "neutralizing antigens" with the T-cell antigen pp65 to expect a marked increase in the immune response (antibody response) compared with the use of the isolated "neutralizing antigen". Examples of such "neutralizing antigens" which should be mentioned are surface proteins of hepatitis B virus (from the HBsAG region), of hepatitis C virus (for example E2), of human immunodeficiency viruses (HIV, from the Env region), of influenza virus (hemagglutinin, neuraminidase, nucleoprotein) or other viral pathogens. Further suitable human pathogens are bacteria such as Haemophilus influenzae, Bordetella pertussis, Mycobacterium tuberculosis, Neisseria meningitidis and others. Finally, antigens from eukaryotic pathogens such as plasmodia (malaria) could be fused to pp65.

In a further preferred embodiment, the particles contain a fusion protein consisting of pp65 and one or more portions of proteins of other pathogens against which CTL are generated in humans on natural infection with these pathogens. Examples of such CTL epitopes which may be mentioned are portions of proteins of HIV-1, of HBV, of HCV or of influenza virus. The intention of such a procedure is to utilize the unique immunogenic properties of DB for generating protective CTL against heterologous pathogens in humans.

In a further preferred embodiment, the particles contain a fusion protein consisting of pp65, of one or more neutralizing epitopes of a heterologous pathogen and of one or more CTL epitopes of the same pathogen. This fusion is intended to ensure that inoculated subjects are able to form both protective antibodies and CTL against this pathogen.

The invention additionally relates to viral particles containing at least 2 different glycoproteins which are variants of the same glycoprotein from different HCMV strains.

A preferred embodiment contains exactly 2 variants, one variant corresponding to the HCMV Towne strain, and the other variant corresponding to the HCMV Ad169 strain. The preferred embodiment contains the glycoprotein gB both of the Towne strain and of the Ad169 strain.

These two proteins can be incorporated with identical efficiency into the membrane of recombinant dense bodies in the infected cell. Such recombinant dense bodies are suitable for inducing not only the strain-overlapping but also the strain-specific neutralizing immune response to the two prototype HCMV strains.

Finally, the invention further relates to a method by which viral particles which are completely free of infectious virus particles are prepared. If particles are produced from a cell population which has been infected with HCMV there is a risk that infectious virus particles will be carried along during the purification of the particles. This represents a disadvantage for a vaccine.

The method of the invention minimizes this risk. To this end, initially an HCMV strain harboring a deletion in an essential gene is produced. By this is meant a deletion of the function of the gene. In most cases, this is based on the absence of a functional gene product, but it is also possible for the function of a regulatory gene sequence to be deranged in such a way that the HCMV is no longer viable. This can take place by altering the nucleic acid sequence of HCMV, for example by point mutations, actual deletions, insertions or other mutations. This defective virus can replicate only in cells which express the gene which has been deleted in HCMV and thus make it available for assembly of the virions. Primary fibroblasts at present represent the only reasonably permissive system for the in vitro replication of HCMV. Stable transfection of such cells has to date been possible only with the aid of retroviral transfer methods. This is, however, a serious disadvantage if such cells are to be used to produce vaccines. The method of the invention makes available stably transfected cells which can be produced without retroviral gene transfer but in which HCMV can also be replicated.

A preferred embodiment comprises human foreskin fibroblasts which have been stably transfected with the major capsid protein gene UL86. The transfection is preferably carried out with a lipid-containing aid which leads to a very high transfection efficiency. In a preferred embodiment, the "Fugene reagent" which can be purchased from Roche Diagnostics, Mannheim, is employed for the transfection. This embodiment is described in example 7.

Defective virus whose major capsid protein gene UL86 has been deleted can be replicated in these cells. If "noncomplementing" fibroblasts are infected with this defective virus, it is then possible to isolate therefrom viral vaccine particles free of infectious virus particles.

Another possibility for producing the particles of the invention without a risk of infection is to reconstitute the particles in cells without infecting with HCMV. To this end, all the genes which code for constituents of the particles must be expressed in these cells. These genes must for this purpose be inserted into the cells.

Insect cells infected by baculoviruses are preferably used for this purpose. The genes which code for the polypeptide constituents of the particles are cloned into baculovirus expression vectors. The production of recombinant baculoviruses is followed by coinfection of insect cells, preferably Sf9 cells, by the various viruses. The genes are expressed in the insect cells, and the resulting polypeptides combine to give the desired particles. Finally, the particles are released by the insect cells. This represents one possibility for producing noninfectious particles which can be used as vaccine.

An alternative possibility is to clone the constituents necessary for reconstitution of DB into recombinant baculoviruses under the control of the HCMV major IE promoter/enhancer (MIEP). It is shown that recombinant baculoviruses are able to infect higher eukaryotic cells such as, for example, mammalian cells, and that foreign genes under the control of a strong eukaryotic promoter such as MIEP are strongly expressed in such cells. The advantage of such a procedure would be that any important modifications, such as glycosylation, of antigenic proteins of the DB could take place in a more natural manner in mammalian cells than in insect cells. In addition, there is a number of such cell lines which are already approved for vaccine production.

Table 1 shows the IgG subclass profile of HCMV-specific antibodies in the serum of balb/cJ mice immunized intraperitoneally at intervals of four weeks with 20 μg of DB each time. The sera were obtained 12 weeks and 32 weeks after the first injection and analyzed as described in example 6. The end point dilution of an assay serum with which the absorption in the ELISA corresponds to 2.5 times the absorption of a zero serum is indicated. The ratio IgG1/IgG2a was determined from these values in each case.

The invention is explained further in the following examples.

EXAMPLE 1

Induction of Neutralizing Antibodies by Native Versus Disrupted DB After a Single Immunization of a Mouse in the Paw Groups of 2 BALB/cJ mice (female, 9–10 weeks old) were immunized either with 2 μg or with 20 μg of purified DB or with 20 μg of disrupted DB by injection into the rear paw. Blood was sampled on day 55 after immunization by cardiac puncture. Serum was obtained by removing the cellular fraction after agglutination.

The mouse sera were investigated for their capacity to neutralize HCMV in the so-called "neutralization assay". The investigation was carried out in accordance with the following protocol:

the sera and the control antibodies 14–4b (neutralizing) and B1B6 (non-neutralizing) were initially prediluted 1:3 in culture medium and then serially diluted ten times, 1:2 each time, in a 48-well plate:
250 μl of each dilution was present.

To each dilution were added 250 μl (same volume) of an HCMV virus stock (Ad169 with a $TCID_{50}$ of $10^{6.3}$/ml (1:200 prediluted 100 μl+19.9 ml) of Dec. 16, 1997) and carefully mixed. The virus had previously been mixed on a "Vortex apparatus" for 20 sec after thawing.

The virus/antibody mixture was incubated in an incubator at 37° C. for 4 h.

After 3.5 h, human foreskin fibroblasts (HFF) which have been released with trypsin were counted and adjusted to $6 \times 10^5$ cells/ml (corresponding to $1.5 \times 10^4$ cells/25 μl).

25 μl portions of cell suspensions were introduced in each case into 4 rows per antibody or antiserum to be assayed in a 96-well plate. After an incubation time of 4 hours, 100 μl portions of the appropriate virus/antibody dilution were added.

This was followed by incubation in a $CO_2$ incubator at 37° C. overnight.

The next day, after the culture supernatant had been discarded, the cultures were fixed with 96% EtOH at –20° C. for 15 min and washed with PBS. Then, the murine monoclonal antibody p63-27; was added as first antibody (50 μl portions per well) and incubated at 37° C. for 1 h.

After renewed washing, the 2nd antibody, an anti-mouse IgG coupled to horseradish peroxidase (Dako, Hamburg, 1:500 in PBS) was added and incubated at 37° C. for 45 min. This incubation was followed by renewed washing with PBS and then an AEC stain was carried out to detect the specific antibody reaction.

For this purpose, 100 μl of an AEC substrate solution are added to each well and incubated in the dark at 37° C. for 10–20 min. The reaction is then stopped with PBS, and the wells are washed several times with PBS. The stained cell nuclei are then identified and counted in transmitted light. Reagents:

AEC stock solution: 400 mg of AEC/100 ml of dimethylformamide (Sigma A-5754)

Acetate buffer: 6.8 g of Na acetate, 2.88 ml of glacial acetic acid, ad 1 l distilled water (pH 4.9)

AEC solution for use: dilute AEC stock solution 1:20 in acetate buffer and filter 2x. Add 1/1000 30% strength $H_2O_2$ shortly before the color reaction.

EXAMPLE 2

Induction of Neutralizing Antibodies by Native DB After Intraperitoneal Immunization of Mice Three Times The induction of antibodies was checked by employing another immunization schedule. For this purpose, 5 animals were immunized intraperitoneally three times (times 0, 4 weeks, 9 weeks) in each case with 20 μg of untreated DB. Blood sampling took place in week 12 for three of the animals and in week 32 for a further two animals.

The mouse sera obtained were investigated for their capacity to neutralize HCMV in the neutralization assay. The method used for this was that described in example 1. The results are depicted below and show that administration of 20 μg of untreated DB three times leads to a significant increase in the neutralizing antibody production compared with a single administration into the paw. The value obtained for the neutralization corresponds to a titer normally obtained with human sera from seropositive donors.

EXAMPLE 3

Induction of a Long-lasting Neutralizing Antibody Response by Native DB After Intraperitoneal immunization of Mice Three Times Balb/cJ mice were immunized intraperitoneally with native DB three times in accordance with the schedule mentioned in example 2. 32 weeks after the first immunization, the serum was obtained from the animals as described above and investigated in the neutralization assay. It emerged that neutralizing antibodies remained detectable in high concentration even after a relatively long time after the initial immunization. This indicates that DB, unlike dead HCMV vaccines used previously, are able to induce a long-lasting neutralizing antibody response.

EXAMPLE 4

Induction of Cytolytic Cells by Native Versus Disrupted DB

The extent to which administration of native and disrupted DB is suitable for activating cytolytic effector cells in the experimental animal was tested in this experimental approach. The method of anti-CD3-mediated redirected lysis was employed for this purpose. The experimental procedure is described below:

Dense bodies were purified from the cell culture supernatant of human foreskin fibroblasts which had been infected with the laboratory strain Ad169 of HCMV at the time of the full cytopathogenic effect (6–8 days after infection). For this purpose, the culture medium was obtained, and viral particles were sedimented by centrifugation in a SW28 rotor at 24,000 rpm (10° C.) for one hour. The sediment was then resuspended in PBS and layered onto a glycerol tartrate gradient. After ultracentrifugation, the bands to be assigned to the dense bodies which were visible in transmitted light were removed using a needle and a 1 ml syringe. An aliquot was checked for purity in an SDS-PAGE, and the amount of DB in the preparation was quantified on the basis of the color intensity, comparing with a BSA standard using the Tina software from Raytest, Germany. To analyze the extent to which the envelope of DB is involved in their immunogenicity, a part of the preparations was treated in such a way that the envelope was separated from the tegument-core structure but the particulate nature of the particles was retained. For this purpose, this portion of the DB was subjected to ten cycles of freezing in liquid nitrogen with subsequent thawing. The particles were then sonicated for 10 minutes in a Branson sonifier (sonifier 250; settings: duty cycle 10%, stage 3—output control 2.5). The structure of the particles treated in this way were visualized under an electron microscope, and their physical properties were analyzed in a sucrose gradient.

The experimental animals employed were female BALB/cJ mice 9–10 weeks old. The mice were immunized by administration of a volume of 50 µl in each case, the material being diluted in PBS, into the right rear paw. 5 groups of animals were immunized, each group consisting of 6 animals. Group 1 was immunized with $2 \times 10^5$ pfu of purified murine CMV (MCMV) in PBS, group 2 with in each case 20 µg of intact dense bodies (quantity in the Coomassie gel standardized to the content of pp65), group 3 with 2 µg of intact dense bodies, group 4 with 20 µg of mechanically damaged dense bodies (see protocol), group 5 with 50 µl of PBS. On day eight, the ipsilateral and contralateral popliteal lymph nodes were dissected. The lymphocytes were isolated by rubbing the lymph nodes through a metal sieve and washing several times. The lymph nodes from a group were pooled. After determination of the cell count, the lymphocytes underwent intermediate cultivation in IL-2-containing medium for eight days (100 U of recombinant human IL-2/ml of T-cell medium). MEM alpha was used as T-cell medium and contained in addition 10% FCS, 4 mM L-glutamine, 100 U/ml penicillin, 0.1 mg/ml streptomycin, 10 µg/ml kanamycin, 10 mM Hepes, 0.00035% β-mercaptoethanol. On day 16, the redirected lysis was carried out. This was done by initially labeling P815 mastocytoma cells (ATCC number: TIB-64; organism: Mus musculus D) with Cr-51. This was done by resuspending $1 \times 10^6$ cells in 30 µl of FCS and labeling with 100 µCi of Cr-51 (sodium dichromate) at 37° C. for 75 minutes. The cells were then washed three times in P815 medium in order to remove excess chromium (P815 medium: RPMI, 10 mM Hepes, 5% FCS, 2 Mm L-glutamine, 100 U/ml penicillin, 0.1 mg/ml streptomycin, 0.00035% β-mercaptoethanol). A part of the cell population was loaded with anti-CD3 antibody: this was done by incubating $5 \times 10^5$ P815 cells with 5 µl of anti-CD3 antibody at room temperature for 15 minutes (hamster anti-mouse CD3ε; Southern Biotechnology Associates Inc. Birmingham, Ala.; 0.5 mg/ml in PBS). The cells were then washed twice.

The cytotoxicity test was carried out in 96-well microtiter plates:

Different quantities of lymphocytes were seeded in 100 µl. 1000 labeled target cells (P815 or P815/anti-CD3) in 100 µl were added to each well. To determine the maximum lysis, 1000 labeled target cells were measured directly in a γ counter. To determine the spontaneous lysis, 100 µl of medium were added in place of effector cells. Centrifugation (100 g, 4 minutes) was followed by incubation at 37° C. for 4 hours. Centrifugation was then repeated (430 g, 4 minutes), and 100 µl of supernatant was removed and its Cr-51 activity was measured in a γ counter. The levels of lysis for the respective effector population are found as follows: (measured chromium release−spontaneous release)×100/maximum release−spontaneous release). The specific redirected lysis is found after subtraction of the levels of lysis determined for the contralateral lymph node cells.

Protocol: mechanical disruption of dense bodies.

The DB were mechanically damaged by freezing and thawing in liquid nitrogen ten times with subsequent sonication in a Branson sonicator for 10 minutes (sonifier 250; settings: duty cycle 10%, stage 3—output control 2.5).

EXAMPLE 5

Induction of pp65-specific CTL After Immunization of HLA-A2.k$^b$ Transgenic Mice The extent to which the administration of native and disrupted DB is suitable for activating HCMV-specific cytolytic effector cells in experimental animals was tested in these experiments. Groups of 8–10 week old mice of the strain C57/BL6, which were transgenic for the human HLA-A2 molecule (C57/BL6-A2.k$^b$), underwent intraplantar immunization as described in example 4 with 2 µg of DB, 20 µg of DB or 20 µg of disrupted DB, dissolved in PBS, without addition of adjuvant. The cells of the popliteal lymph nodes were obtained as described, counted and cultivated in T-cell medium in vitro with addition of 100 U/ml recombinant human interleukin-2 for 8 days. On day 16, the HCMV-specific cytolytic activity in these cell populations was measured. The target cells employed for the chromium release test were human T2 cells (ATCC CRL-1992) and Jurkat cells (ATCC number TIB-152) which stably expressed the gene for the chimeric MHC molecule A2.k$^b$. The cells were labeled with Cr-51 as described in example 4. Then portions of $5 \times 10^5$ cells were loaded on the one hand with a known pp65 peptide presented by HLA-A2 (amino acids 495–503; peptide prepared synthetically by Jerini, Berlin), and on the other hand with an irrelevant control peptide, presented by HLA-A2, from the tumor suppressor protein p53 (amino acids 149–157). For this purpose, the peptides were dissolved in a concentration of $10^{-3}$M in PBS and then further diluted in decimal steps. Portions of $5 \times 10^5$ target cells were then incubated in a volume of 500 µl with peptides in a final concentration of $10^{-5}$ to $10^{-10}$M at 37° C. for 1 h. The unbound peptides were then removed by washing in T-cell medium. The optimal peptide concentrations for loading the two T cell lines had been determined in preliminary tests to be $10^{-6}$M for Jurkat cells and $10^{-8}$M for T2 cells.

Figure 1:
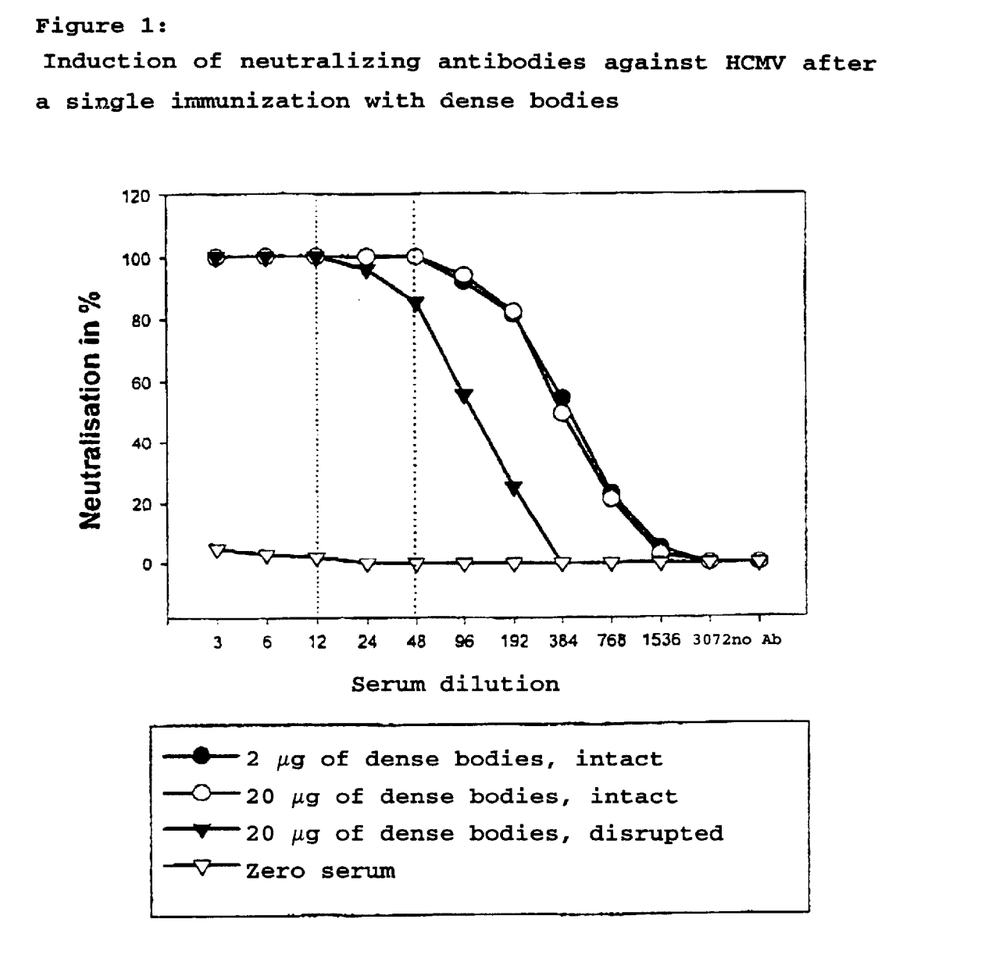
FIG. 1 shows the result of the neutralization assay for detecting HCMV-neutralizing antibodies in the sera of mice after a single immunization with dense bodies preparations according to example 1. Neutralization is assessed as 100% if a positive cell nucleus is no longer detectable in the four-fold mixture in the staining method described in example 1 (broken lines). The degree of neutralization at a particular serum dilution emerges from the number of positive cells in the four-fold mixture relative to the number of positive cells in the mixture without antibody.
Figure 2:
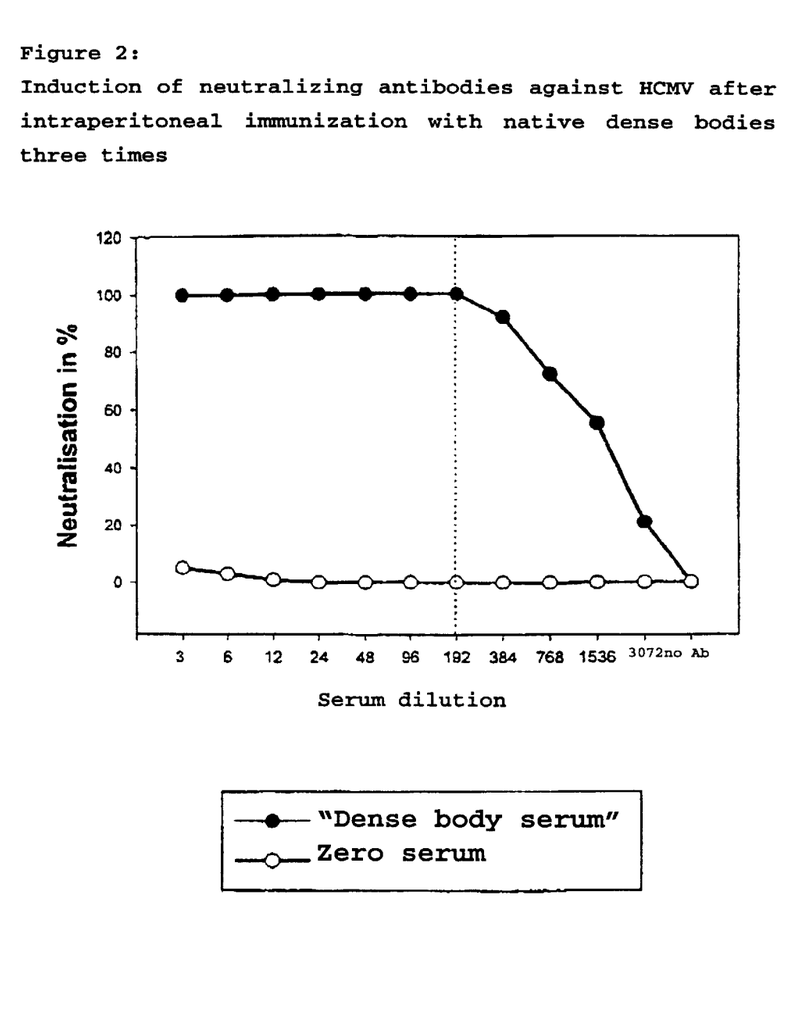
FIG. 2 shows the result of the neutralization assay for detecting HCMV-neutralizing antibodies in the sera of mice after intraperitoneal immunization three times, each 4 weeks apart and each with 20 µg of native dense bodies as described in example 2. The assay was evaluated as described in FIG. 1. The dotted line indicates the serum titer at which there was 100% neutralization. The "zero serum" employed was the serum from a mouse not immunized with HCMV particles.
Figure 3:
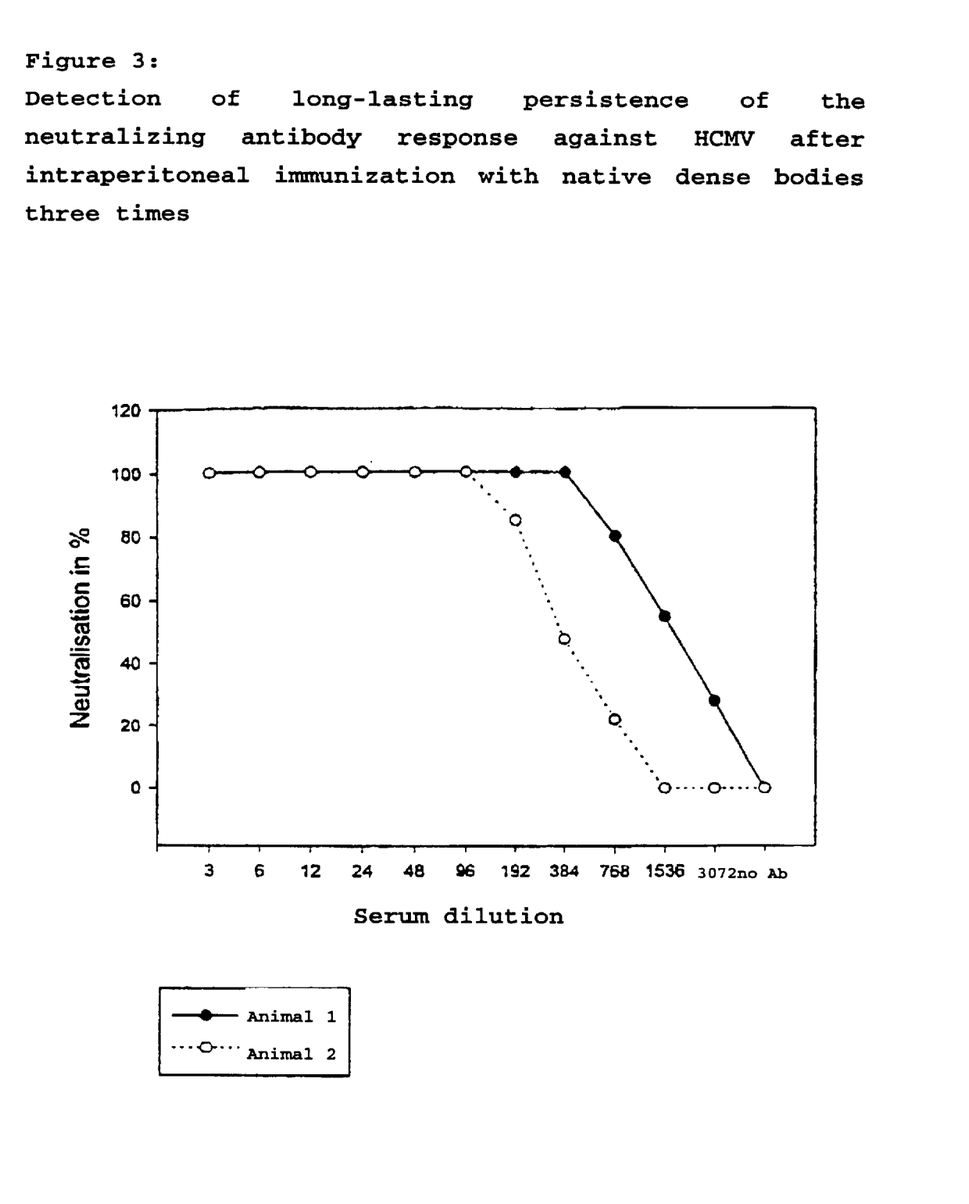
FIG. 3 shows the result of a neutralization assay for detecting a long-lasting production of neutralizing antibodies after intraperitoneal immunization three times (4 weeks apart) each with 20 µg of native dense bodies as in example 3. The evaluation took place as described in FIG. 1.
Figure 4:
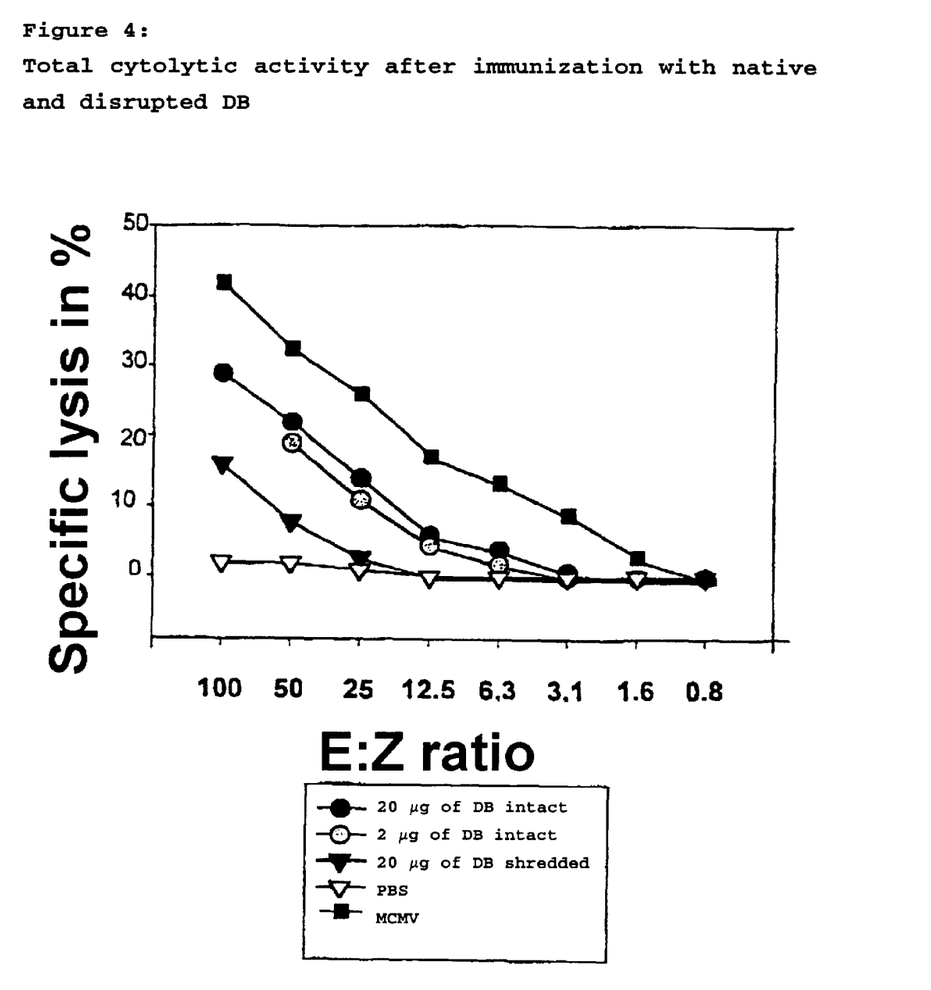
FIG. 4 shows the result of an analysis of the total cytolytic activity after immunization of mice with native and disrupted dense bodies with the aid of anti-CD3ϵ-mediated redirected lysis, as described in example 4. The lytic activity observed in each case is plotted against the ratio of effector cells to target cells.
Figure 5:
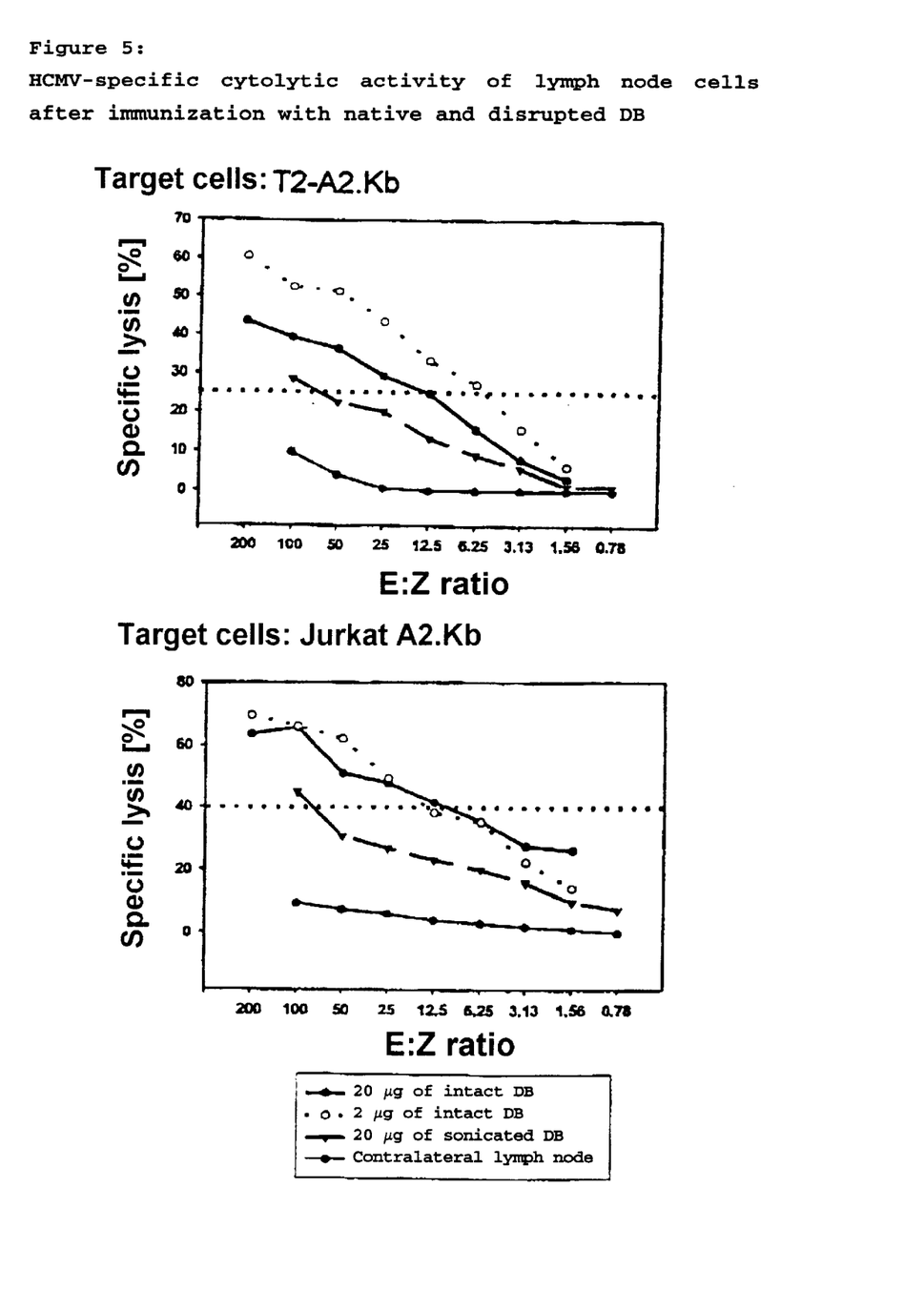
FIG. 5 shows the result of an analysis of the HCMV-specific cytolytic activity of lymph node cells after immunization with native and disrupted DB, as described in example 5. The lytic activity observed in each case, measured by the extent of the release of radiolabeled chromium, is plotted against the ratio of effector cells to target cells employed (E:Z ratio). The dotted lines mark by way of example the relative number of effector cells necessary to achieve a preset level of lysis. It is evident that it was necessary to employ distinctly smaller numbers of cells from animals immunized with untreated DB in order to reach the same level of lysis.

Chromium release tests were carried out with a decreasing effector cell: target cell (E:T) ratio (FIG. 5). For this, the values for chromium release obtained in a parallel experiment after loading of the target cells with an irrelevant peptide (peptide presented by HLA-A2 from the tumor suppressor protein p53) were subtracted from the values obtained in each case after specific lysis of target cells loaded with the pp65 peptide. It emerged that immunization with DB had led to generation of pp65-specific (HCMV-specific) CTL. Moreover, the cells of the animals immunized with 2 µg of DB showed somewhat higher values for chromium release at a preset E:T ratio than the cells of the animals immunized with 20 µg of DB. Although the cells of the animals immunized with disrupted particles still showed pp65-specific cytolysis, the chromium release, as a measure of their cytolytic effector activity, was distinctly lower, at the given E:T ratio, than that of the cells from animals which had received untreated DB. In particular, at a preset chromium release value as a measure of the cytolytic activity of the cells obtained from animals treated with disrupted particles, the relative number of effector cells necessary for this (E:T ratio) was distinctly higher. Taken together, these results indicate that (I) immunization of experimental animals with the "dead antigen" DB is suitable for generating HCMV-specific cytolytic T cells and that (II) the efficiency of the cellular immune response depends on the cellular uptake of DB, presumably mediated by an intact envelope. This result must be said to be exceptionally remarkable because an efficient generation of CTL against intracellular pathogens is usually dependent on the de novo synthesis of the corresponding antigens in the cell. The "exogenous loading", mediated by DB, of the MHC class I complex with virus-specific peptides can thus be regarded as exceptionally efficient and ought to be suitable for generating protective cytotoxic effector functions against HCMV and against heterologous pathogens such as, for example, influenza virus.

EXAMPLE 6

Immunization With DB Leads to an Induction of a Th1-typical T-helper Cell Response Induction of a permanent humoral and cellular immune response depends crucially on whether and in what way T-helper lymphocytes can be induced. On immunization against viral pathogens it is particularly desirable to generate a Th1-typical immune response. In order to check the extent to which immunization with DB is suitable for this purpose, two different experimental approaches were chosen.

Figure 6:
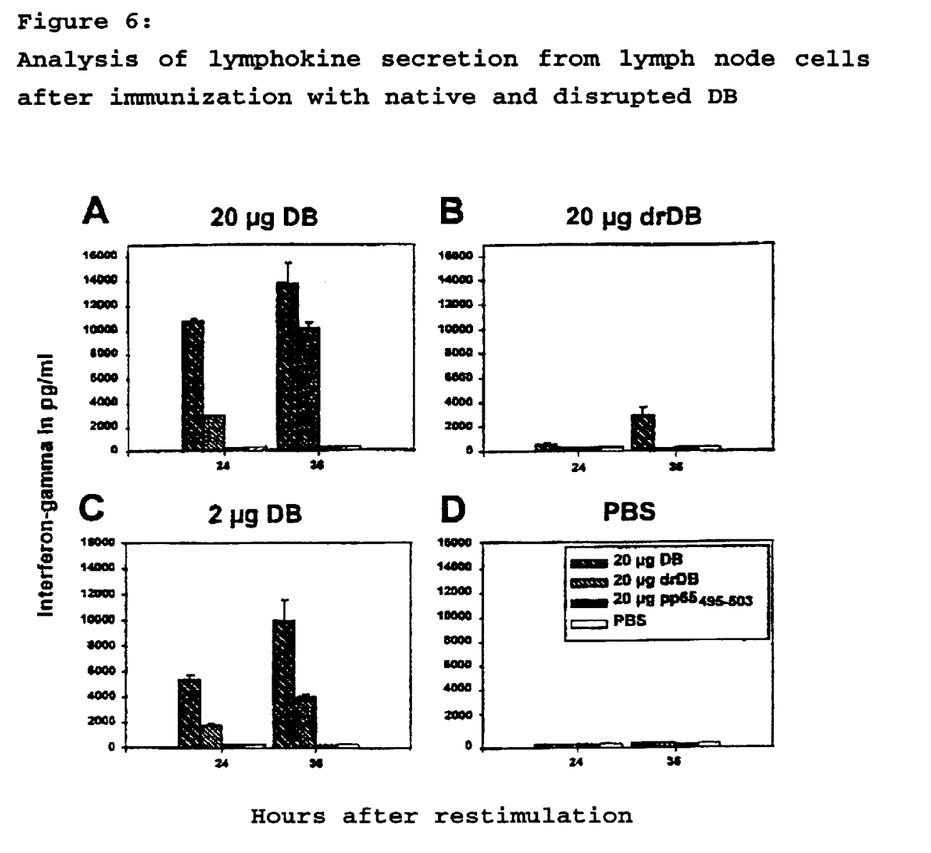
FIG. 6 shows the result of an analysis of the nature of the Th immune response after immunization with native and disrupted DB based on the lymphokine release by lymph node cells, as described in example 6. The amount of IFN-γ released is plotted against the time after restimulation. A) immunization with 20 µg of DB, B) immunization with 20 µg of disrupted DB (drDB), C) immunization with 20 µg of DB, D) immunization with PBS (negative control). The antigens employed for the restimulation are shown in the insert in D). IL-5 secretion was determined in parallel. Significant secretion of IL-5 was not detectable in any case.

In a first experimental approach, it was tested whether lymph node cells from experimental animals which had undergone intraplantar immunization with DB synthesize and release, after intermediate cultivation, Th1-typical (in this case: interferon-$\gamma$, IFN-$\gamma$) or Th2-typical (in this case interleukin-5, IL-5) lymphokines. Groups each of six Balb/cJ mice underwent intraplantar immunization with 2 $\mu$g of DB, 20 $\mu$g of DB, 20 $\mu$g of disrupted DB dissolved in PBS or with PBS alone. Lymph node cells were obtained after 8 days after immunization as described in example 4 and were seeded in a density of $10^6$ cells/ml in RPMI 1640 medium supplemented with 2 mM L-glutamine, 100 U/ml penicillin, 0.1 mg/ml streptomycin, 5% (v/v) FCS, $5 \times 10^{-5}$ M 2-mercaptoethanol, 10 mM Hepes. The cells were restimulated in culture with either 20 $\mu$g of DB, 20 $\mu$g of disrupted DB, with a peptide (pp65, 495–503) presented by MHC class I (HLA-A2) or with PBS by adding these antigens to the culture medium. 24 and 36 hours after restimulation, the cell culture supernatant was harvested and centrifuged in an Eppendorf centrifuge at 2 500 rpm for 10 min in order to remove cell residues. The content of IFN-$\gamma$ and IL-5 in the supernatant from the culture cells was measured using commercially available ELISA test kits (Endogen, Woburn, U.S.A.) (FIG. 6). To standardize the measurement values, recombinant IFN-$\gamma$ and IL-5, which were also supplied in the same test kits, were dissolved in the cell culture medium used and also analyzed in parallel.

The lymphocytes from the animals immunized with 20 $\mu$g or 2 $\mu$g of DB secreted large amounts of IFN-$\gamma$. Distinctly less IFN-$\gamma$ was secreted by cells from animals immunized with disrupted particles. IL-5 was not measured in significant quantity in any mixture. These results indicate that immunization of experimental animals with DB is suitable for inducing a Th1-typical immune response and that the extent of the induction in turn depends on the integrity of the DB membrane.

Since it is known that induction of a Th1-typical or Th2-typical immune response depends inter alia on the form of administration, in a second experimental approach mice were immunized intraperitoneally with 20 $\mu$g of DB three times at an interval of 4 weeks. Whole blood from the animals was obtained after 12 and 32 weeks after the first injection by cardiac puncture under ether anesthesia, incubated at 37° C. for 2 h for agglutination, stored at 4° C. overnight and, the next day, centrifuged at 14 000 rpm for 10 min. The clear serum supernatant was removed and stored in small aliquots at −20° C. The content of HCMV-specific immunoglobulins of subclasses IgG1 and IgG2a in the sera was determined. During a Th1-typical immune response there is preferential formation of IgG2a class antibodies, whereas with a Th2-typical immune response antibodies of the IgG1 class predominate. Sera from the experimental animals were inactivated at 56° C. for 30 min and tested using a commercially available ELISA, coated with the antigens of extracellular HCMV particles (Biotest AG, Dreieich). For this purpose, serial dilution series of the test sera were prepared, pipetted into the wells of the ELISA plate and incubated at 37° C. for 2 h. After 3 washing steps in PBS/0.05% Tween 20, the subclass-specific, HRP-coupled secondary antibody was added in a dilution of 1:2 000 in PBS/2% Tween 20/3% FCS and incubated at 37° C. in a moist atmosphere for 1 h. A further 4 washing steps were followed by an OPD color reaction, which was stopped by adding 100 $\mu$l of 0.5M $H_2SO_4$. The absorption at a wavelength of 492 nm was then measured in an ELISA reader.

A regression line was drawn through the values for the absorption for the various dilutions of a serum, and the value corresponding to 2.5 times the absorption of a zero serum was found as so-called "endpoint dilution". The ratio of the endpoint dilutions for IgG1:IgG2a afforded a quotient which was always below 0.3, irrespective of the immunization protocol (table 1). Since IgG1:IgG2a quotients <1 indicate a Th1-typical immune response, whereas quotients >1 indicate a Th2 response, this experiment proves that the immunization with DB induces a Th1-like T-helper cell response. Analogous results were obtained in a parallel experiment with intraplantar administration of DB. This shows that, irrespective of the mode of administration, the immunization with DB leads to a Th1-typical immune response of the experimental animals.

EXAMPLE 7

Technique for Expressing Heterologous Genes in Primary Human Fibroblasts and Complementation of Defective Mutants of HCMV in Such Cells Human fibroblasts with the minimum number of passages are seeded on 6-well plates, employing $10^5$ cells in each case. A cover glass is introduced into some of the wells beforehand for control purposes.

The cells are incubated in a $CO_2$ incubator at 37° C. overnight and transfected the next day. The desired transgene is expressed, for example, on the plasmid pcDNA6/V5-His (Invitrogen) which also harbors the blasticidin S deaminase gene. Expression of this gene confers resistance to the substance blasticidin S.

An alternative possibility is for the desired transgene to be transfected to a separate expression plasmid together with the vector pRG273 which confers resistance to the antibiotic puromycin. This vector is a derivative of the vector pLXSN16E6E7 and, besides the resistance gene, expresses the transforming proteins E6 and E7 of human papillomavirus 16. This can increase the growth potential of the relevant cells by transformation thereof.

The transfection is carried out by the "Fugene method" of Roche Diagnostics. For this purpose, 3 µl of Fugene reagent are mixed with 97 µl of medium without FCS and incubated at room temperature for 5 minutes. In about 2.5 µg of DNA of the transgene plasmid (plus 50 ng of pRG273 in the case of double transfections) are added and, after a further 15 minutes at room temperature, 900 µl of serum-containing medium are added. After removal of the old medium, this mixture is added to the cells. The transfection takes place for 3–8 hours. After this, the transfection mixture is removed and culture medium is added. After cultivation for 2 days, the cover glasses are transferred into 24-well plates, washed and fixed with 90% acetone. Expression of the transgene is checked by indirect immunofluorescence microscopy with the aid of antibodies.

If the transfection efficiency is satisfactory, the remaining cells are released with trypsin and seeded in selection medium (e.g. 3 µg/ml blasticidin, 2 µg/ml puromycin, 250 µg/ml G418 etc.). If cell colonies form in the selection medium, they are isolated and cultivated further under selection conditions. The cells are subsequently expanded under selection conditions, and the strength of expression of the transgene is checked for example in an immunoblot. If the expression is satisfactory, the cells are divided into aliquots and stored in liquid nitrogen until used further.

EXAMPLE 8

Strategy for Generating Recombinant DB Containing Fusion Proteins of pp65 With Homologous or Heterologous Antigens A possible strategy for producing recombinant DB is as follows:
starting from the genomic DNA fragment BamHI-R (cloned into pBluescribe as pBamHIR) of the Ad169 strain, initially plasmid clones which contain heterologous nucleic acid sections cloned into a unique SrfI cleavage site in the 3' portion of the pp65 gene are produced. The coding DNA regions for various antigenic sections of HCMV proteins other than pp65 or of proteins of other pathogens are cloned in such a way that a continuous open reading frame with UL83 (pp65) results. In the 3' direction relative to these heterologous DNA sections it is possible to clone, likewise in the continuous reading frame, a fusion gene consisting of the gene for the so-called green fluorescent protein (GFP) and of neomycin transferase. This gene is to be selected in each case by a recognition site for Cre recombinase (LoxP sites) of the phage P1. The plasmid constructs resulting from this are depicted in FIG. 7.

The recombinant plasmids are transfected into human foreskin fibroblasts. These cells are superinfected with the HCMV Ad169 strain. Homologous recombination results in recombinant HCMV genome molecules which contain the respective fusion gene in place of pp65. Addition of G418 to the culture medium selects for replication of these recombinant DNA molecules and for concentration of recombinant viruses. The expression of GFP additionally makes it possible to use cytofluorometry (FACS) for positive sorting of cells which contain recombinant viral genomes. Efficient concentration and subsequent isolation of recombinant viruses is ensured in this way.

The purified viruses are then passaged through cell lines which transiently or stably express CRE recombinase. This recombinase recognizes a short sequence of base pairs (loxP sites) in a DNA molecule, and excises exactly the DNA sections located between such loxP sites. This results in deletion of the DNA sections which were used for the selection and which code for GFP-Neo. Selection of GFP-negative cells in the FACS is followed by isolation and purification of pure virus which expresses a pp65 fusion protein for the selection.

Pure virus populations can subsequently be employed for infecting human fibroblasts. During the virus infection, recombinant DB are produced in these infected cells and can subsequently be purified from the cell culture supernatant in turn by gradient centrifugation.

It is possible to produce, for example, the following viruses (see FIG. 7):

A) Viruses which express a fusion protein consisting of pp65 and known neutralizing domains from the gB of HCMV. Domains of this type have been referred to in the literature as AD1 and AD2. The homologous domain to AD2 from the gB of the Towne laboratory strain has been referred to as TW2.

B) Viruses which express a fusion protein consisting of pp65 and known CTL epitopes of the IE1 protein (IE1) of HCMV.

C) Viruses which express a fusion protein consisting of pp65, of known neutralizing domains of HCMV glycoprotein (NA) and of known CTL epitopes of the IE1 protein ((IE1)) of HCMV.

D) Viruses which express a fusion protein consisting of pp65 and of known CTL epitopes of other pathogens such as, for example, of the nucleoprotein of influenza A virus (for example AA 147–155).

E) Viruses which express a fusion protein consisting of pp65, of known neutralizing epitopes (NA) of another pathogen and of known CTL epitopes (CTL) of this other pathogen.

What is claimed is:

1. Viral particles released after infection of mammalian cells by human cytomegalovirus (HCMV), wherein a) the particles are surrounded by a lipid membrane in which viral glycoproteins are embedded, b) the particles contain neither viral DNA nor capsids, c) the particles contain a fusion protein comprising one or more parts of the T-cell antigen pp65 (UL83) and one or more parts of one or more proteins, which are not pp65.

2. The particles of claim 1, wherein the T-cell antigen pp65 (UL83) is fused to one or more parts of an HCMV glycoprotein.

3. The particles of claim 1, wherein the T-cell antigen pp65 (UL83) is fused to one or more parts of the HCMV glycoprotein gB.

4. The particles of claim 1, wherein the T-cell antigen pp65 (UL83) is fused to one or more parts of the HCMV glycoprotein gH.

5. The particles of claim 1, wherein the T-cell antigen pp65 (UL83) is fused to one or more parts of the HCMV protein IE1 (ppUL123).

6. The particles of claim 1, wherein the T-cell antigen pp65 (UL83) is fused one or more parts of an HCMV glycoprotein and to one or more parts of the HCMV protein IE1 (ppUL123).

7. The particles of claim 1, wherein the T-cell antigen pp65 (UL83) is fused to one or more parts of a protein, which is part of a human pathogen other than HCMV.

8. The particles of claim 1, wherein the fusion protein comprises at least one epitope against which neutralizing antibodies are formed in humans upon infection, and at least one other epitope against which CTL are formed in humans upon infections, the epitopes being derived from proteins of the same pathogen.

9. The particles of claim 1, wherein cytotoxic T lymphocytes (CTL) are formed in humans against the protein which is part of a human pathogen other than HCMV upon natural infection with the pathogen.

10. The particles of claim 9, wherein the other human pathogen which is not HCMV is selected from the group consisting of HIV-1, HBV, HCV and influenza.

11. The particles of claim 9, wherein the fusion protein comprises at least one epitope of a protein of a human pathogen other than HCMV, neutralizing antibodies against the epitope being formed in humans upon infection, and at least one other epitope of a protein of the other human pathogen, CTL against the other epitope being formed in humans upon infection.

12. Viral particles released after infection of mammalian cells by HCMV, wherein
   a) the particles are surrounded by a lipid membrane in which viral glycoproteins are embedded,
   b) the particles contain neither viral DNA nor capsids,
   c) the particles contain gB and/or gH protein antigenic fragments which are from different HCMV strains.

13. The particles of claim 12, wherein the strains are one of the 2 variants: HCMV Towne strain and HCMV Ad169 strain.

14. The particles of claim 12, wherein the glycoprotein is the gB protein of HCMV.

* * * * *